United States Patent [19]

Droege

[11] Patent Number: 5,399,017

[45] Date of Patent: * Mar. 21, 1995

[54] METHOD AND APPARATUS FOR EVALUATING HEAT EXCHANGER EFFICIENCY

[76] Inventor: Thomas F. Droege, 2 S. 942 Thorncrest La., Batavia, Ill. 60510

[*] Notice: The portion of the term of this patent subsequent to Sep. 28, 2010 has been disclaimed.

[21] Appl. No.: 116,035

[22] Filed: Sep. 2, 1993

Related U.S. Application Data

[63] Continuation-in-part of Ser. No. 932,709, Aug. 19, 1992, Pat. No. 5,248,198.

[51] Int. Cl.$^6$ .................... G01N 25/20; G01M 19/00
[52] U.S. Cl. ........................................ 374/7; 165/11.1
[58] Field of Search ............... 374/7, 43, 208; 73/112; 165/36, 11.1

[56] References Cited

U.S. PATENT DOCUMENTS

| | | |
|---|---|---|
| 2,330,599 | 9/1943 | Keuhni . |
| 2,951,360 | 9/1960 | Sampson et al. . |
| 3,075,377 | 1/1963 | Lang . |
| 3,095,739 | 7/1963 | Doolittle .................. 374/41 X |
| 3,724,267 | 4/1973 | Zoschak . |
| 3,913,378 | 10/1975 | Hausler ........................ 374/7 |
| 3,918,300 | 11/1975 | Weisstuch .................. 374/7 X |
| 4,024,751 | 5/1977 | Potrzebowski .............. 374/43 |
| 4,527,908 | 7/1985 | Arisi ............................ 374/147 |
| 4,722,610 | 2/1988 | Levert et al. ............... 374/43 |

FOREIGN PATENT DOCUMENTS

| | | |
|---|---|---|
| 855658 | 12/1960 | United Kingdom . |
| 1423830 | 2/1975 | United Kingdom . |
| 1403950 | 8/1975 | United Kingdom . |
| 741126 | 6/1980 | U.S.S.R. . |

OTHER PUBLICATIONS

Dats Fouling Monitor System; *Bridger Scientific, Inc.,* (Date Unknown).
Cooling Water Fouling Monitor Senses Upsets, Evaluates Changes; Zunige, et al., *Chem. Proc.* pp. 34–38 (Apr. 1990).

*Primary Examiner*—Diego F. F. Gutierrez
*Attorney, Agent, or Firm*—Allegretti & Witcoff, Ltd.

[57] ABSTRACT

A method for evaluating the type, extent, and threshold of fouling in a heat exchanger test tube by using a reference test block to measure a reference thermal relaxation time at a guaranteed clean reference section of a heat exchanger test tube and comparing the reference thermal relaxation time with thermal relaxation times measured at the bottom region of unclean sections of the heat exchanger test tube.

7 Claims, 2 Drawing Sheets

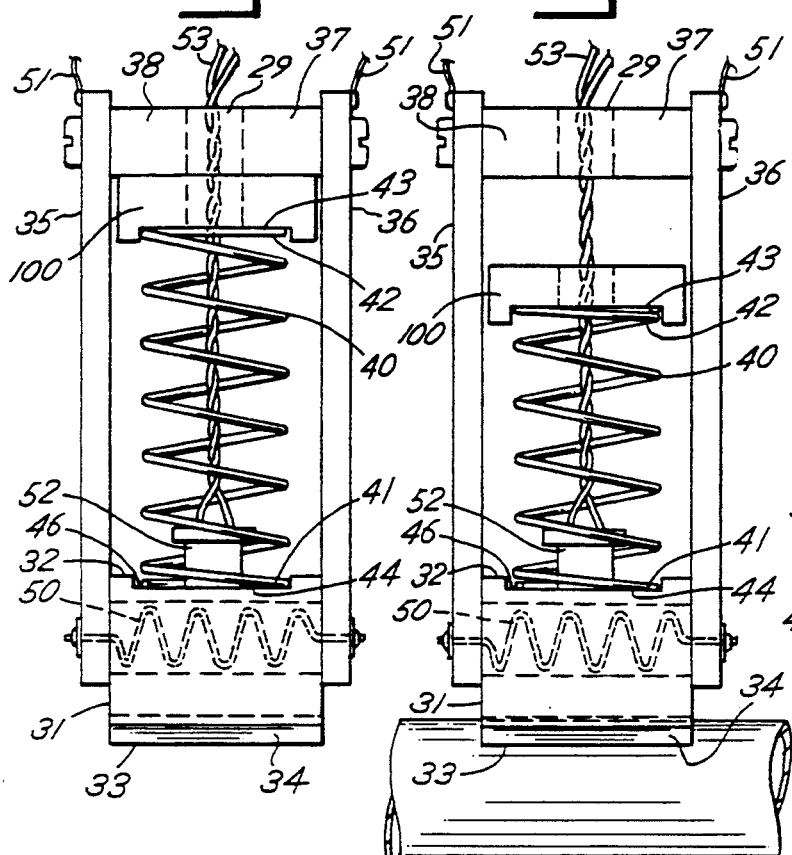

METHOD AND APPARATUS FOR EVALUATING HEAT EXCHANGER EFFICIENCY

This application is a continuation-in-part of U.S. patent application Ser. No. 07/932,709, filed on Aug. 19, 1992, now U.S. Pat. No. 5,248,198.

BACKGROUND OF THE INVENTION

I. Field of the Invention

The present invention pertains to methods and an apparatus useful for determining the type, extent of, and thermal threshold of fouling in heat exchanger elements. The apparatus of this invention is capable of being easily installed and removed from the simulated side arm of various types of heat exchangers thereby facilitating the evaluation of the heat exchanger fouling.

In thermodynamic apparatuses, such as heat exchangers, condensers, and the like, the formation of corrosion products, mineral, and organic deposits from various heating or cooling media can, over time, impair the thermal transmission or thermal resistance of the heat exchanger elements. The formation of corrosion products, mineral deposits, and organic deposits can be counteracted by intermittently cleaning the heat exchanger or through the controlled addition of fouling inhibiting additives to the heat exchange media. Cleaning the heat exchangers or chemical addition can be very expensive. To reduce these expenses, heat exchanger tubes are monitored to establish the presence of and the magnitude of fouling materials, and to evaluate the effectiveness of chemical addition. As a result of the monitoring, manual cleaning or chemical addition can be efficiently controlled.

The methods presently used to evaluate heat exchanger tube fouling rely greatly on balancing the flow rate of the heat exchange media through multiple heat exchanger test tubes. The methods produce inaccurate results when the flow rate of the heat exchanger media is unbalanced. Additionally, the monitorial methods presently used are generally incapable of identifying the type foulant.

II. Description of the Art

U.S. Pat. No. 2,330,599, to Kuehni, describes the basic principles for evaluating the thickness of a material using a thermal testing apparatus. The patent describes a thermal conductivity testing apparatus that includes a heat source and two resistance elements. One resistance element is placed into contact with a plate and the other is left uncontacted. The difference in the temperatures of the two resistance elements is monitored. The rate at which the temperature of the resistance monitor in contact with the plate decreases correlates to the thickness of the plate it touches.

Other patents also describe similar methods of measuring the thermal conductivity of fluids and other materials. These patents include United Kingdom Patents 1,423,830, 1,403,950, and 855,658. The '658 patent describes an apparatus for measuring the thermal conductivity of a test material using two probes mounted within an insulated block where one probe is contacted with the test material while the other probe remains isolated from the test material. The '830 patent describes an apparatus and method for measuring heat flux using a single probe. A single probe is exposed to a heat flux and the rate at which the probe increases in temperature is measured. The '950 patent describes a method for measuring the thermal diffusivity of a sample by exposing a first surface of a sample to heat or radiation source while maintaining a second surface of a sample at a constant temperature. When the first surface is exposed to a heat or radiation pulse, the power necessary to maintain the second surface of a sample at the desired temperature is reduced. The power consumption is then correlated with the heat or radiation pulse magnitude to determine the thermal diffusivity of the sample.

U.S. Pat. No. 2,951,360 describes a method and apparatus for testing the thermal conductivity of materials. The method and apparatus are useful for testing the quality of metal welds.

U.S. Pat. No. 3,724,267 describes a heat flux sensing device. The device includes two thermocouples located at two different locations along the length of a conductor. The thermocouples sense a temperature gradient from which a heat flux can be determined.

U.S. Pat. No. 4,024,751 describes an apparatus for determining the heat transfer efficiency of a heat exchanger wall. The '751 patent recognizes that the efficiency of a heat exchanger is diminished by build up of materials and scale on heat exchanger wall surfaces. The claimed apparatus evaluates the magnitude of scale build up by heating the wall of a heat exchanger tube from first pre-determined temperature to a second pre-determined temperature, halting the heating, and measuring the time it takes for the temperature of the measured portion of the heat exchanger wall to drop from the second predetermined temperature to the first predetermined temperature. The amount of time it takes to return from the second temperature to about the first temperature can be correlated to heat exchanger scale accumulation. The apparatus disclosed is a permanent apparatus including a heating means in direct contact with a heat exchanger tube.

U.S. Pat. No. 4,722,610 describes a monitor for determining the build up of slag on the flame side of water cooled walls of a coal-fired steam generator. The monitor includes a heater located adjacent to a thermocouple in a body. The thermocouple usually monitors the temperature of the body and when the body temperature decreases, this is an indication of slag build up. This indication is confirmed by heating the body with the heater, and measuring the temperature drop of the body using the same thermocouple. A slow drop in the temperature of the body indicates a large build up of slag.

Other apparatuses and methods for evaluating heat exchanger performance are known. However, the art lacks a method that uses a guaranteed clean reference as the basis for evaluating heat exchanger fouling.

SUMMARY OF THE INVENTION

A principle object of this invention is to provide a method for measuring heat exchanger performance that is useful in evaluating whether heat exchanger fouling is due to sedimentation, organic material build-up, or due to inorganic material build-up.

Another object of this invention is to provide a method for identifying the onset of fouling in a heat exchanger by determining whether or not fouling exists in the bottom region of a heat exchanger test tube.

This invention relates generally to a method for evaluating fouling in a heat exchanger test tube containing a flowing fluid. According to one aspect of the method, a reference test block including a heater and a thermometer is contacted with a clean reference section of the heat exchanger test tube. The test block is heated to a temperature above that of the flowing fluid. The reference test block is allowed to cool providing a measurement of a reference thermal relaxation rate. Next, a measuring test block including a heater and thermometer is contacted with the bottom region of an unclean section of the heat exchanger test tube. The measuring test block is heated to a temperature above that of the flowing fluid and then allowed to cool. As the measuring test block cools, a measured thermal relaxation time is determined. The degree of fouling in the unclean section of the test tube is then determined by comparing the reference thermal relaxation time and the measured thermal relaxation time.

Another method of this invention is useful for determining the fouling thermal threshold. This method uses a reference test block and one or more measuring test blocks. The reference test block is used to measure the reference thermal relaxation time at a clean section of the test tube. A measuring test block is contacted with the bottom region of an unclean section of the test tube, i.e., a section of the test tube that has been operated at a heat load, and is maintained at a temperature above that of the flowing fluid. Occasionally, the heater heating the measuring test block is shut off and the actual relaxation time corresponding to the unclean section is measured. The thermal threshold of fouling, is found by measuring a series of thermal relaxation times when the measuring test block has been heated to various temperatures greater than the temperature of the flowing fluid. Thermal relaxation times indicating a decrease in fouling with increased temperature indicates the fouling due to organic deposits. Thermal relaxation times which indicate that fouling is increasing at increasing heater block temperatures indicates that a fouling is a result of non-organic materials and these readings can be used to identify the temperature at which fouling will begin.

DESCRIPTION OF THE DRAWINGS

There is shown in the drawings a presently preferred embodiment of the invention wherein like numerals in the various figures pertain to like elements and wherein;

FIG. 3 and 3A are front views of a test assembly prior to and in contact with a test tube;

FIG. 4 is a side view of a test block assembly of this invention in contact with a test tube;

FIG. 5 depicts a mechanical device for producing a clean reference point in a test tube; and FIG. 6 depicts a chemical method for producing a clean reference point in a heat exchanger test tube.

DESCRIPTION OF THE CURRENT EMBODIMENTS

Figure 1:
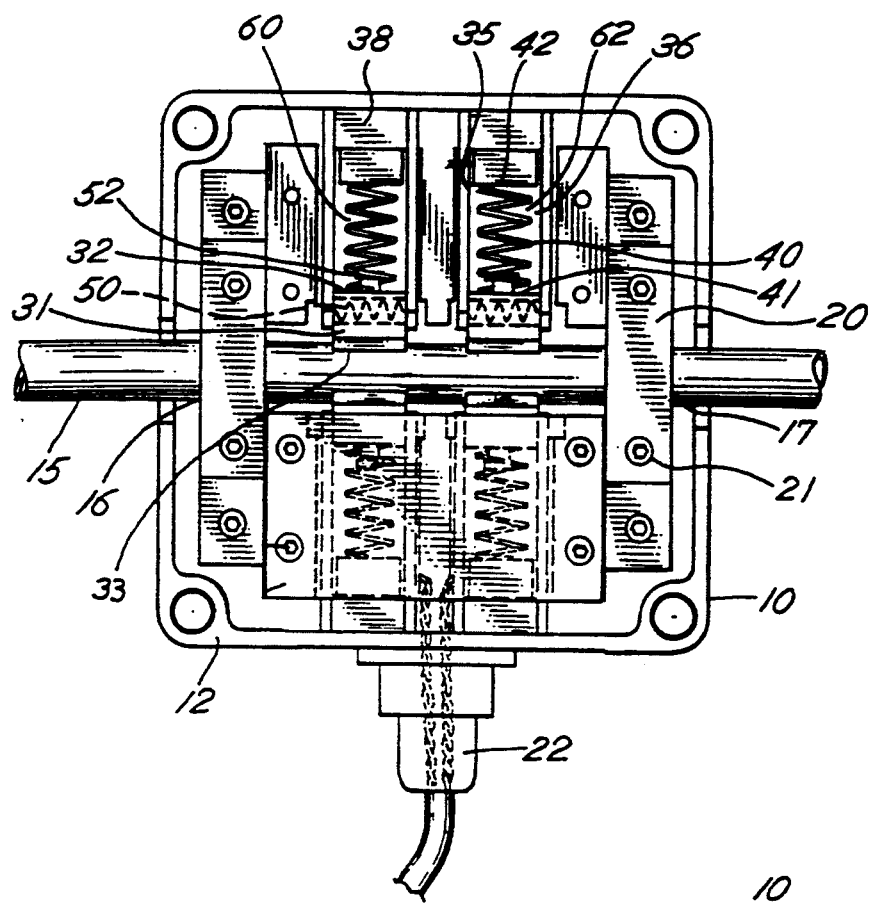
FIG. 1 is a front view of the portable monitor of this invention.

The present inventions relates to a method for determining the extent, type, and thermal threshold of fouling in heat exchanger tubes. The method utilizes a guaranteed clean reference measuring point. The guaranteed clean reference measuring point allows for the measurement of a reference thermal relaxation time in a heat exchanger test tube. The reference thermal relaxation time is then compared to thermal relaxation times measured at unclean points in the heat exchanger test tube in order to evaluate heat exchanger fouling.

A thermal relaxation time is essentially the time it takes for a heated block, in intimate contact with a heat exchanger test tube to drop from a first predetermined temperature, T1, above that of the fluid flowing in the heat exchanger test tube to a second predetermined temperature T2. Both T1 and T2 are greater than the temperature of the fluid in the heat exchanger test tube. The reference thermal relaxation time and the measured thermal relaxation time are compared. Typically, a change in ratio between the reference and measured thermal relaxation times can be correlated to fouling in the heat exchanger.

The thermal relaxation time is related to the ability of the heat exchanger tubes to transfer heat energy. As the thermal relaxation time is being measured, the fluid in the heat exchanger test tube is removing the heat in a heated test block in intimate contact with the test tube causing the temperature of the test block to decrease. If the exchanger test tube is fouled, the fouling material provides resistance to this heat flow and the thermal relaxation time increases. Knowledge of the exact extent of the heat exchanger fouling is important when chemicals are being used to minimize heat exchanger fouling. By periodically determining thermal relaxation times, the ability of the chemical addition to inhibit or reduce existing heat exchanger fouling can be evaluated, and adjusted.

One problem encountered by measuring thermal relaxation times at an unclean section of a heat exchanger test tube is that the efficiency of the chemical addition, the minimum amount of chemicals needed to produce the desired result, cannot be measured. It is, of course, most desirable to inhibit heat exchanger fouling using the least amount of chemicals. Another problem suffered by current heat exchanger monitors is that they requirement that fluid flow rates be balanced through test tubes when a plurality of test tubes are used to measure the efficiency of chemical addition. The method of this invention eliminates the problems associated with unclean measuring points and the need to balance flow rates where multiple test tubes are used.

The method of this invention measures a reference thermal relaxation time at a section of the heat exchanger test tube that is guaranteed clean, i.e., where no fouling exists. At the guaranteed clean reference point, the thermal relaxation time is constant assuming all other process variables are constant. However, if flow rate temperature, or flow composition of the flowing fluid change, then the reference thermal relaxation time will also change. One method to correct for changes in process variables is to electronically determine a flow rate in the heat exchanger test tube by using the reference thermal relaxation time. With the exact flow rate of the fluid in the heat exchanger test tube known, the measured thermal relaxation times can be corrected for flow rate differences to get a corrected thermal relaxation times which can be compared to previous measured thermal relaxation times to determine actual heat exchanger fouling. An alternate method is to periodically measure and update the reference thermal relaxation time.

The method of this invention can be used to determine the extent, type, and thermal threshold of heat exchanger fouling. The extent of heat exchanger fouling is determined using at least two test blocks, a reference test block and at least one measuring test block. The reference test block includes a thermometer and a heater. The reference test block is placed into intimate contact with the heat exchanger test tube such that the reference test block contacts as much of the surface of the heat exchanger test tube as is possible. The reference test block is placed into intimate contact with the heat exchanger test tube so that the reference test block contacts a controlled and unchanging section of the heat exchanger test tube. The counting for the test block (shown in FIG. 1) allow the test block to freely move into square alignment with the test tube. The actual contact area is not critical, it is only critical that the contact area is fixed over the life of the measurement. This is accomplished by designing the test blocks so that they are free to "float" into alignment with the test tube, and not contact the test tube in cocked manner, that is, touching the test tube only at a point or a line. The effect of any imperfections in the surface of the test block or test tube is minimized by applying thermally conductive grease to the contact area.

The measuring test block is placed into intimate contact with an unclean portion of the heat exchanger test tube. When referring to a portion of the heat exchanger test tube as unclean, it is not meant that there is fouling in that section of the heat exchanger test tube. What is meant by the term "unclean," is that particular section of the heat exchanger test tube has not been cleaned in any way to guarantee that there is no fouling in that particular section.

A reference thermal relaxation time is measured by heating the reference test block, which is in intimate contact with the guaranteed clean section of the heat exchanger test tube to a temperature above that of the fluid flowing in the heat exchanger test tube. The reference test block is heated with the heater associated with the reference test block. The heating of the reference test block is discontinued and the temperature of the test block is allowed to drop. The thermal relaxation time then is the time it takes for the reference test block to cool from a predetermined temperature T1 to a predetermined temperature T2 with both T1 and T2 being above the test tube temperature. Ultimately, if allowed to cool completely, the reference test block will reach an equilibrium temperature about equivalent to the temperature of the flowing fluid in the test tube.

Next, the thermal relaxation time for an unclean portion of the heat exchanger test tube is measured. The measuring test block is heated with its integral heater to a temperature above that of the fluid flowing through the heat exchanger test tube. The heating of the measuring test block is discontinued and the measuring test block is allowed to cool. The thermal "measured" relaxation time of the measuring test block is then determined by determining the time it takes for the measuring test block to drop in temperature from a high predetermined temperature T1 to a low predetermined temperature T2. The reference and measured thermal relaxation times may be determined simultaneously or sequentially. It is preferred that the thermal relaxation times are determined simultaneously. The thermal relaxation times may be simultaneously determined as long as the test tube flow rate is high enough or the measuring points spaced far enough apart so that the measuring points are essentially thermally insulated from one another.

At this point the thermal relaxation time for the unclean portion of the heat exchanger test tube can be corrected for flow rate differences and other variables to define a corrected thermal relaxation time. The corrected thermal relaxation time can then be compared to other corrected thermal relaxation times or to the reference thermal relaxation time to determine whether fouling is present in the heat exchanger and the effect of the fouling in heat exchanger efficiency.

The method above is useful in determining the extent of fouling in the heat exchanger. Chemical addition to the heat exchanger can be modified in order to reduce or eliminate the fouling thereby increasing the efficiency of the heat exchanger. Subsequent measurements of reference thermal relaxation times and measured thermal relaxation times may be made to evaluate any changes in chemical addition.

A slightly different method is used to determine the type of fouling. There are at least two types of fouling that can be identified by methods of this invention. One type of fouling that can be identified is sedimentation fouling. With sedimentation, gravity causes particles in the flowing fluid to settle onto the bottom region, (in the direction of gravitational forces), of the heat exchanger test tube. This buildup of sediments on the bottom region of the heat exchanger test tube is in contrast to the top or opposite region of the test tube which is relatively free of foulants. Therefore, sedimentation can be identified by placing a first measuring test block into intimate contact with the top region of a heat exchanger testing tube and a second measuring test block into intimate contact with the bottom region of a heat exchanger testing tube. In this situation, where the thermal relaxation time of the top region is being compared to the thermal relaxation time of the bottom dimension, a reference thermal relaxation time is not absolutely necessary. However, a reference relaxation time will always be necessary to correct the measured thermal relaxation times, so that they can be compared with measured thermal relaxation times taken at different fluid flow conditions To determine if sedimentation exists, a reference test block including a heater and a thermometer is contacted with the clean reference section of the heat exchanger test tube. The reference thermal relaxation time is then measured by heating the reference test block to a temperature above that of the flowing fluid, discontinuing the heating, and measuring the time it takes for the reference test block to decrease from a high predetermined temperature T1 to a lower predetermined temperature T2.

Next, a first measuring test block including a heater and thermometer is placed into intimate contact with the top region of an unclean section of the test tube while a second measuring test block including the heater and a thermometer is placed into intimate contact with the bottom region of the unclean section of the test tube. The first and second measuring test blocks are then heated sequentially, or in unison to a temperature above that of the fluid flowing in the heat exchanger test tube. The heating of the first and second measuring test blocks is then discontinued and time it takes for the first and second measuring test blocks to decrease in temperature from a first predetermined temperature T1 to a second predetermined temperature T2 is measured to obtain a first thermal relaxation time and a second thermal relaxation time. The first and second thermal relaxation times can then be compared, and if the second thermal relaxation time is much greater than the first thermal relaxation time then sedimentation fouling is indicated. The first thermal relaxation time and the second thermal relaxation times can also be corrected to obtain corrected first and second thermal relaxation times. The corrected thermal relaxation times can be compared with previous data to determine if there is any change in the fouling characteristics of the heat exchanger test tube.

It has also been discovered that heat exchanger tube fouling, besides sedimentation, may exhibit itself first as scale build up on the bottom region of heat exchanger test tube. Therefore measuring thermal relaxation rates on the bottom region of an unclean portion of a heat exchanger test tube is important in order to quickly identify the onset of heat exchanger fouling. The term "bottom region" refers to the portion of the heat exchanger test tube closest to the earth or some other primary source of gravity.

In order to identify the onset of fouling, one or more measuring test blocks are contacted with the bottom region of the heat exchanger test tubes, and relaxation times are measured as previously described. The reference test block may, but need not be associated with the bottom region of a clean reference section of the test tube. The orientation of the reference test block is not critical because all dimensions of the clean reference section should be scale and sediment free.

The presence of organic foulants and the threshold foulant temperature can both be determined in a similar manner. However, the indications for each are not the same. The presence of organic foulants is indicated by a reduction in measured thermal relaxation times with increasing test block temperatures. On the other hand, the threshold temperature for fouling is determined by increasing the measuring test block temperature until the measured thermal relaxation times indicate an increase in fouling.

The method for evaluating the presence of organic foulants or determining the threshold fouling temperature begins by contacting a reference test block including a heater and a thermometer with a clean reference section of the heat exchanger test tube. A reference thermal relaxation time is then measured. Next, a measuring test block including a heater and a thermometer is placed into intimate contact with an unclean section of the test tube and the measuring test block is heated to a first test temperature above that of the flowing fluid. The first thermal relaxation time is then measured by discontinuing the heating of the measuring test block and measuring the time it takes for the measuring test block to decrease in temperature from a predetermined temperature T1 to predetermined temperature T2. Next, the measuring test block is heated to a second test temperature greater than the first test temperature and a second thermal relaxation rate is measured. The measuring test block is then heated to a third test temperature above that of the second and a third thermal expansion time is measured. This process of increasing the test temperature and measuring thermal expansion times is repeated until the thermal relaxation rate increases, indicating the beginning of fouling, or decreases indicating that organic foulants are being swept away from the walls of the heat exchanger test tube. In this method, it is the heated, moveable test block that actually causes or eliminates the fouling.

A second way to determine organic fouling is by the time development of the fouling. Scale formation tends to take long periods of time to develop significant change in heat transfer. Organic fouling on the other hand can be quite rapid. Therefore dramatic changes in thermal relaxation in hours are possible when the conditions become favorable for organic growth. Organic growth is also temperature sensitive, with optimum temperatures for different organic foulants being well known. With several blocks heated to temperatures known to be favorable for particular types of organic growth, it is possible to determine the type of organism and thus the optimum chemical treatment.

Another method for determining the presence of organic foulants or the threshold fouling temperature is to use a reference test block in conjunction with a plurality of measuring test blocks. The reference test block is used to measure a reference thermal relaxation time while the plurality of measuring test block are kept in intimate contact with unclean portions of the heat exchanger test tube. The plurality of measuring test blocks are each continuously kept at temperatures above the temperature of the fluid flowing through the heat exchanger test tube. For example, if five measuring test blocks are contacted with the heat exchanger test tube then the first test block might be ten degrees above the fluid temperature, the second measuring test block twenty degrees above the fluid temperature, the third measuring test block kept at thirty degrees above the fluid temperature and so on. To evaluate the threshold fouling temperature or type of foulant, the thermal relaxation time for each of the plurality measuring test blocks is simultaneously or sequentially determined. A difference in the thermal relaxation time of one or more of the measuring test blocks will indicate the presence of organic foulants or the threshold fouling temperature. Based on these measurements, chemicals may be added or removed from the flowing fluid to promote heat exchanger efficiency.

The test blocks do not cool exactly as an ideal, first order system does. In the simple first order case, the time constant is the time it takes for the temperature to drop to $1/e$ ($e=2.718$) of the difference between its initial and its final temperature. For example, suppose the test block is heated to 100 degrees above the water temperature. Time 1 would be the time when the test block is at 100 degrees and the heater has turned off. Time 2 would be when the test block reaches ($100/e$) or 36.78 degrees.

Unfortunately the test blocks do not behave exactly as first order systems. There is usually a range over which a test block will behave similarly to a first order system. The advantage of the first order system is that the same measurement is obtained regardless of the temperatures between which the two time measurements are taken, so the measurement accuracy does not change as the time constant changes with fouling. The first order system is by definition the longest time constant. By waiting a while after the heater is turned off to mark the first temperature and time 0, the effects of higher order (faster) terms is minimized. It is preferred that the first time be measured after the temperature has dropped to 90% of the difference between the maximum heater block temperature and the test tube temperature and the second time be measures at $90 \cdot (1/e)$. The purpose of this measurement is to make the time constant measurement independent of the temperature or temperature difference. Thus T1 and T2 might be different for each of the blocks measured. But the ratios of T1 and T2 to the temperature difference of the particular block measured are the same for all the measured blocks. Normally $T1/T2=e$. But it might be $0.73 \cdot e$ or $0.20 \cdot e$; any ratio would work.

The test tube may be cleaned by various means to produce a guaranteed clean heat exchanger test tube section. The cleaning may be done mechanically, chemically or ultrasonically. A mechanical means for cleaning a section of the test tube is shown in FIG. 3. FIG. 5 shows heat exchanger test tube 10 having an elbow. The reference test block 60 is located above a clean portion of test tube 10 while the measuring test block 62 is located above an unclean portion of test tube 10. The test tube 10 is cleaned using brush 65 which can be manually pulled back and forth in a section of the test tube using handle 66. Test tube 10 can be cleaned while fluid is flowing by virtue of seal 67 which prevents liquid from escaping test tube 10.

A chemical method for producing a guaranteed clean section of test tube 10 is shown in FIG. 6. Fluid typically flows through test tube 10 when first valve 70 and second valve 72 are opened. To clean the portion of test tube 10 associated with reference block 60, first valve 70 and second valve 72 are closed and third valve 73 and fourth valve 74 are opened. An acidic solution or some other cleaning solution is flushed through a portion of test tube 10 via third valve 73 and passes out of the test tube via fourth valve 74 to guarantee a clean test tube section for reference test block 60. The test tube section associated with measuring test block 62 is not cleaned.

A third method for producing a guaranteed clean reference section of the heat exchanger test tube is an ultrasonic cleaner associated with the reference test block. The ultrasonic cleaner can be intermittently or continuously operated to clean any foulants off the inner dimension test tube in the area where test block is in intimate contact with the test tube.

By no means are the methods for producing a guaranteed clean section of heat exchanger test tube mentioned above exclusive. Any other methods in the art for cleaning only a section of a tube while leaving the remaining section of the tube unclean within the scope of this invention.

The present method is preferably accomplished using a portable monitor that is capable of monitoring heat exchanger efficiency using a clean reference. The portable monitor of this invention is better understood by reference to FIGS. 1, 2, 3, and 3A which show various aspects of a preferred portable monitor and test block assembly of this invention.

Figure 2:
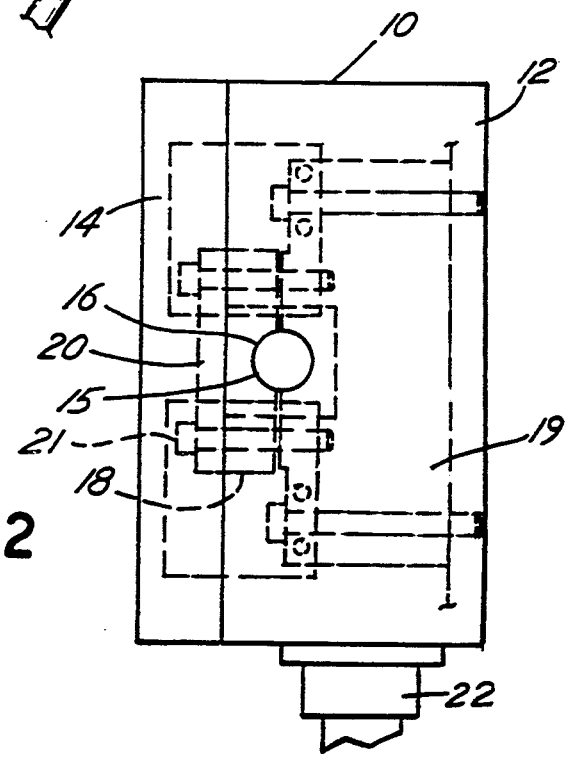
FIG. 2 is a side view of the portable monitor of this invention.

FIGS. 1 and 2 show front and side views respectively of the portable monitor of this invention. The portable monitor includes housing 10 comprising box 12 and box cover 14. FIG. 1, the front view of the portable monitor, shows the housing 10 with box cover 14 removed so that the contents of the housing are exposed. Housing 10 includes a first aperture 16 and a second aperture 17. The apertures may be located in the box 12 or in the box cover 14. A first aperture 16 and second aperture 17 located on opposite sides of the housing to define opposing apertures.

First aperture 16 and second aperture 17 provide a location where a test tube 15 can pass through housing 10 unimpeded. A test tube 15 is a standard feature on many heat exchangers. The test tube 15 mimics conditions occurring in the tubes contained in a multitube heat exchanger. The conditions that are mimicked include fluid temperature, fluid flow rate, fluid composition, and fluid pressure. Instead of being located in the heat exchanger, however, test tube 15 is located external to the heat exchanger. The portable monitor of this invention can be attached to test tube 15 in order to monitor the heat exchanger efficiency.

Housing 10 also includes supports 18 complementary to the first aperture 16 and the second aperture 17 for fixedly attaching the portable monitor of this invention to test tube 15. Supports 18 include a fixed support 19 which is attached to the housing and removable support 20 which is attached by fasteners 21 to fixed support 19. Fixed support 19 and removable support 20 include concave depressions on the dimension of the fixed support 19 and removable support 20.

An electrical connector 22 is integral to housing 10. Electrical connector 22 electrically links heaters, thermometers, and other electrical devices in housing 10 to a source of electricity or to temperature or heater displays.

The purpose of housing 10 is to protect the test block assemblies 30 enclosed by the housing from the external environment. Housing 10 protects the test block assemblies 30 from tampering, from spills, and from other hazards that could potentially damage the test block assemblies or that could affect the accuracy of the data collected from the test block assemblies. The housing 10 can be purged with an inert gas if the test block assembly is located in an area that might be prone to explosions.

One or more test block assemblies 30 are enclosed in housing 10. Each test block assembly 30 includes a movable test block 31 having a flat face 32 and a concave face 33. Movable test block 31 is located between parallel side supports which include a first side support 35 and a second support side 36. A spring support 38 is oriented perpendicularly to the parallel side supports and is fixedly attached to one extreme of first and second parallel side supports 35 and 36. A spring 40 is attached at first end 41 flat face 32 of movable test block 31. A second end 42 of spring 40 is attached to spring support 38. The spring 40 urges movable test block away from spring support 38.

Test block assembly 30 is secured to housing 10. Generally the spring support 38 will be attached to box 12 with some type of fastener such as a screw, a bolt, or some other fastener. When attached to housing 10, spring support 38 is generally immobile. First side support 35 and second side support 36 are perpendicularly attached to spring support 38 such that the first side support 35 and second side support 36 form parallel side supports. The first side support 35 and second side support 36 are fastened to spring support 38 such that the parallel side supports are essentially immobile.

First side support 35 and second side support 36 are manufactured of a thin rigid material. The side supports act to guide the movement of movable test block 31. The side supports prevent movable test block 31 from moving laterally in relation to test tube 15. It is preferred that first side support 35 and second side support 36 are made of circuit board materials and are in fact themselves printed circuit boards. When the parallel side supports are circuit boards, they may include printed circuits for electrically uniting a heater 50, and thermometer 52 to heater leads and thermometer leads. The leads can then pass into electrical connector 22 which protects the leads outside of housing 10, and which unites the leads with a source of electricity and/or monitoring devices.

Movable test block assembly 30 is located in-between the parallel side supports 34. Movable test block is attached to spring support 38 by spring 40. Spring 40 has a first end 41 which is fixedly attached to the flat face 32 of movable test block 31. Spring 40 also has a second end 42 which is fixedly attached to the spring support 38. The spring biases movable test block 31 away from spring support 38.

Movable test block 31 also has a concave face 33 opposite flat face 32. Concave face 33 contacts test tube 15 such that essentially the entire concave face 33 of movable test block 31 contacts a complementary convex surface of test tube 15. It is possible that test tube 15 will have a non-circular cross-section. In such a situation, the movable test block will not have a concave face but will have a face that is complementary to the geometry of test tube 15. However, it is preferred that test tube 15 have a circular cross-section and, as a result, the movable test block 31 will have a concave face.

The movable test block serves at least two purposes. The movable test block is made of a thermally conductive material that can be quickly heated to a desired controlled temperature. The movable test block also must remain in intimate contact with test tube 15 or to measure the ability of test tube 15 to remove heat from movable test block 31. Additionally, movable test block 31 can contain a thermometer 52. The conductive nature of movable test block 31 along with the fact that it is in intimate contact with test tube 15 ensures that the movable test block 31 will, except when heated, be at a temperature essentially identical to the temperature of the fluid in test tube 15.

Movable test block 31 can be made from any known conductive material. The best conductive materials are metals with a preferred conductive material being silver.

Movable test block 31 may include a heater 50, a thermometer 52, or both a heater and a thermometer. A preferred heater 50 is a resistance type heater which is generally located in a hole drilled through movable test block 31 parallel to test tube 15. Heater 50 is preferably attached by a heater lead to a printed circuit board which acts as one of the parallel side supports. Movable test block 31 can also include a thermometer 52. A preferred thermometer is a solid state semi-conductor transistor Model AD-590 manufactured by Analog Devices. Thermometer 52 is typically attached to flat face 32 of movable test block 31. A thermometer lead may unite thermometer 52 with a circuit board acting as a parallel side support 34. Alternately, the thermometer lead can pass through a hole in the spring support and run directly to electrical connector 22.

The portable monitor of this invention is attached to test tube 15 to monitor the efficiency of a heat exchanger associated with the test tube. In order to attach the portable monitor to a test tube, the box cover 14 must be removed from housing 10 to expose box 12 and one or more test block assemblies 30 located inside box 12. The fasteners 21 uniting removable support 20 with fixed support 19 are removed and removable support 19 is detached from support 18. Box 12 is oriented such that test tube 15 rests on the concave faces of the fixed support 19. Removable test blocks 31 are consecutively urged by hand or by some other means towards spring support 38 and then released to allow spring 40 to urge each movable test block 31 away from spring support 38 and into intimate contact with test tube 15. When each concave face 33 of each movable test block 31 is contacting test tube 15, the concave dimension of each removable support 20 is contacted with the corresponding convex dimension of test tube 15 and fastened to fixed support 19 to define support 18. Support 18, when assembled, prevents housing 20 from rotating about test tube 15. Box cover 14 is finally attached to box 12 to define housing 10.

The portable monitor of this invention may include two or more test block assemblies 30 having movable test block 31 which includes a heater 50 and a thermometer 52. Preferably, one test block assembly will be the reference test block assembly including the reference test block. The remaining test block assembly or assemblies will be measuring test block assemblies. Measuring test block assembly includes a measuring test block for measuring the thermal relaxation time of an uncleaned section of a heat exchanger test tube. Alternatively, a plurality of portable monitors may be used to measure various thermal relaxation times.

The description above has been offered for illustrative purposes only, and it is not intended to limit the scope of the invention of this application which is defined in the following claims.

What I claim is:

1. A method for evaluating fouling in a heat exchanger test tube containing a flowing fluid comprising the steps of:
    (a) contacting a reference test block including a heater and a thermometer with a clean reference section of the test tube;
    (b) measuring a reference thermal relaxation time by heating the reference test block with the reference test block heater to a temperature greater than that of the fluid passing through the test tube, discontinuing the heating of the reference test block, and measuring the time it takes for the reference test block to cool from a first predetermined temperature, T1, to a second predetermined temperature, T2;
    (c) contacting at least one measuring test block including a heater and a thermometer with a bottom region of an unclean section of the test tube;
    (d) measuring a measured thermal relaxation time of the unclean section of the test tube by heating the measuring test block with the measuring test block heater to a temperature greater than that of the fluid passing through the test tube, discontinuing the heating method measuring test block, and measuring the time it takes for the measuring test block to cool from the first predetermined temperature, T1, to the second predetermined temperature, T2; and
    (e) determining the degree of fouling in the unclean section of the test tube from the reference thermal relaxation time and the measured thermal relaxation time.

2. The method of claim 1 wherein the degree of fouling in the unclean section of the test tube is determined in step (e) by comparing the reference thermal relaxation time with the measured thermal relaxation time.

3. The method of claim 1 wherein the degree of fouling in the unclean section of the test tube is determined in step (e) by comparing a plurality of measured thermal relaxation times, taken with a plurality of measuring test blocks, with the reference thermal relaxation time.

4. The method of claim 1 wherein the reference test block is contacted with the bottom region of the reference section of the test tube.

5. The method of claim 1 wherein the second predetermined temperature T2 is equal to T1(1/e), where e=2.718.

6. A method for evaluating fouling in a heat exchanger test tube containing a flowing fluid comprising the steps of:

(a) contacting a first test block including a heater and a thermometer with a clean reference section of the test tube;

(b) measuring a reference thermal relaxation time by heating the reference test block with the heater to a temperature above that of the flowing fluid, discontinuing the heating and measuring the time it takes for the reference test block to cool from a first predetermined temperature, T1, to a second predetermined temperature, T2;

(c) contacting a plurality of measuring test blocks each including a heater and a thermometer with the bottom region of unclean sections of the test tube;

(d) heating the plurality of measuring test blocks with their respective measuring test block heater such that each of the plurality of measuring test blocks is at a different temperature and all of the measuring test blocks are at a temperature greater than the temperature of the flowing fluid;

(e) maintaining the respective temperatures reached in step (d) of the plurality of measuring test blocks;

(f) measuring a thermal relaxation time for each of the plurality of measuring test blocks by discontinuing the heating to each of the plurality of measuring test blocks and measuring the time it takes for each of the plurality of measuring test blocks to cool from the first predetermined temperature, T1, to the second predetermined temperature, T2; and (g) determining a degree of fouling in the unclean section of the test tube from the reference thermal relaxation time and the plurality of measured thermal relaxation times.

7. The method of claim 6 wherein a threshold fouling temperature is determined by comparing each of the plurality of thermal relaxation times measured in step (f) with the reference thermal relaxation time.

* * * * *